(12) United States Patent
Edlauer et al.

(10) Patent No.: US 8,187,847 B2
(45) Date of Patent: May 29, 2012

(54) **PROCESS FOR PRODUCING ERYTHRITOL USING *MONILIELLA TOMENTOSA* STRAINS IN THE PRESENCE OF NEUTRAL INORGANIC NITRATES, SUCH AS POTASSIUM NITRATE, AMMONIUM NITRATE OR SODIUM NITRATE, AS NITROGEN SOURCE**

(75) Inventors: Robert Edlauer, Thaya (AT); Stefan Trimmel, Thaya (AT)

(73) Assignee: Jungbunzlauer Austria AG, Vienna (AT)

( * ) Notice: Subject to any disclaimer, the term of this patent is extended or adjusted under 35 U.S.C. 154(b) by 555 days.

(21) Appl. No.: 12/443,060

(22) PCT Filed: Oct. 1, 2007

(86) PCT No.: PCT/AT2007/000457
§ 371 (c)(1), (2), (4) Date: Mar. 26, 2009

(87) PCT Pub. No.: WO2008/040036
PCT Pub. Date: Apr. 10, 2008

(65) Prior Publication Data
US 2009/0246843 A1  Oct. 1, 2009

(30) Foreign Application Priority Data

Oct. 3, 2006 (AT) ................. A 1646/2006

(51) Int. Cl.
*C12P 7/18* (2006.01)
*C12P 7/02* (2006.01)
(52) U.S. Cl. ........................... 435/158; 435/171
(58) Field of Classification Search .......... None
See application file for complete search history.

(56) References Cited

U.S. PATENT DOCUMENTS

| 4,923,812 | A |   | 5/1990 | Horikita et al. |
|---|---|---|---|---|
| 5,534,243 | A | * | 7/1996 | Dixon et al. ............ 424/49 |
| 5,902,739 | A | * | 5/1999 | Abe et al. ............ 435/158 |
| 6,030,820 | A |   | 2/2000 | Morioka et al. |

FOREIGN PATENT DOCUMENTS

| EP | 0136803 A2 | 10/1985 |
|---|---|---|
| EP | 0327342 A2 | 8/1989 |
| EP | 0845538 B1 | 12/1996 |
| JP | 47-41549 | 12/1972 |
| JP | 60110295 A | 6/1985 |
| JP | 1199584 A | 8/1989 |
| JP | 5121072 A | 5/1993 |

OTHER PUBLICATIONS

Rosa et al. Synonymy of the yeast genera *Moniliella* and *Trichosporonoides* and proposal of *Moniliella fonsecae* sp. nov. and five new species combinations. International Journal of Systematic and Evolutionary Microbiology (2009)), 59, 425-429.*

G. Hasselbeck, W. Henke; Erbsloeh-Weinkompendium Enzyme; Erbsloeh Geisenheim Getraenketechnologie; D-65366 Geisenheim; p. 14. Relevance is that it was cited on p. 1 of the instant application.

L. Hanssens, A. Van Regenmortel and H. Verachtert; PH—Dependent Polyol Production in *Moniliella tomentosa*; Applied Microbiology; Nov. 1972, p. 831-833; University of Louvain, Haverlee, Belgium. Relevance is that it was cited on p. 2 of the instant application.

Diano et al.; Polyol Synthesis in *Aspergillus niger*: Influence of Oxygen Availability, Carbon and Nitrogen Sources on the Metabolism; Biotechnology and Bioengineering of Aug. 5, 2006, p. 899-908; DTU, Biocentrum, Center for Microbial Biotechnology, Lyngby, Denmark; published online on May 22, 2006 in Wiley InterScience (www.interscience.wiley.com) DOI: 10.1002/BIT.20915, p. 903-904. Relevance is that it was cited on p. 3 of the instant application.

Lee, Kwang-Jun et al; Optimized Conditions for High Erythritol Production by *Penicillium* sp KJ-UV29, Mutant of *Penicillium* sp. KJ81; Biotechnology and Bioprocess Engineering 8(3), 173-178 (2003); Laboratory of Respiratory Infections, National Institute of Health, Seoul, 122-020. South Korea. Relevance is that it was cited on p. 3 of the instant application.

* cited by examiner

*Primary Examiner* — Cynthia Collins
(74) *Attorney, Agent, or Firm* — Paul & Paul

(57) ABSTRACT

The present invention relates to the use of at least one inorganic nitrate in a fermentation process for producing erythritol using a yeast strain of the *Moniliella* species as an erythritol-producing microorganism characterized in that the at least one inorganic nitrate is simultaneously used as a main nitrogen source and as a pH regulator in the culture medium, as well as to such an improved method for producing erythritol.

8 Claims, No Drawings

PROCESS FOR PRODUCING ERYTHRITOL USING *MONILIELLA TOMENTOSA* STRAINS IN THE PRESENCE OF NEUTRAL INORGANIC NITRATES, SUCH AS POTASSIUM NITRATE, AMMONIUM NITRATE OR SODIUM NITRATE, AS NITROGEN SOURCE

This invention relates to an improved method for producing erythritol by recovery from the culture medium of a microorganism culture.

PRIOR ART

Numerous methods for producing erythritol by microorganisms, especially yeasts, are known in the art, wherein various nitrogen sources are used. JP-A 47-41549, for example, describes the use of a casein hydrolysate as a nitrogen source for strains of the species *Trigonopsis* and *Candida*. JP-A 51-21072 discloses the use of yeast extract and urea for different yeast strains.

JP-A 60-110295 and JP-A 1-199584 each describe the use of *Moniliella tomentosa* var. *pollinis* for producing erythritol. Since this variety is known to have high nutrient demands, culture media known for use therewith usually have a high content of complex nitrogen sources such as yeast extract, peptone, corn steep liquor or similar high-protein substances of plant or animal origin. Thus, in JP-A 60-110295 and JP-A 1-199584 corn steep liquor, urea and yeast extract are used as nitrogen sources.

However, these complex nitrogen sources do not only constitute a decisive cost factor, but also complicate purification of the erythritol formed and reduce the yield after crystallization. Consequently, considerable efforts have been undertaken to reduce the portion of complex nitrogen sources as far as possible. This may be achieved by using organic nitrogen sources such as urea or inorganic salts such as ammonium sulfate. Since considerable amounts of ethanol are formed during the fermentation of erythritol, the use of urea leads to problems due to the possibility of ethyl carbamate formation, which is rated as cancerous (G. Hasselbeck, W. Henke; Erbsloeh-Weinkompendium Enzyme; Erbsloeh Geisenheim Getraenketechnologie; D-65366 Geisenheim; p. 14).

Thus, EP 0,845,538 B1 and its German translation DE 697 20 379 T2, which deal with this problem, disclose the combined use of ammonium sulfate, an inorganic salt, and corn steep liquor, wherein the first is called "main nitrogen source" and constitutes 50 to 85% of the nitrogen sources, while the latter constitutes the remaining 15 to 50%. Yeast strains mentioned besides *Monoliella* (also "*Monoliella pollinis*") are members of the species *Yarrowia* and *Trichosporonoides*. One process step described is adjusting the pH to values between 3 and 7 (see also claim 12 therein). An optional usability of potassium nitrate as a nitrogen source is mentioned in a table as a general example.

Of course, it has been known since 1985 from EP 0,136, 802 A that polyol formation by *Moniliella tomentosa* var. *pollinis* proceeds in a desirable manner under a pH ranging from 3 to 6, preferably a pH ranging from 4 to 5. The effects of the pH value on the polyol yield were described in 1972 by L. Hanssens, A. van Regenmortel and H. Verachtern (Applied Microbiology, November 1972, p. 831-833).

Thus, the use of ammonium sulfate described in EP 0,845, 538 B1, which is a salt of a very strong dibasic acid ($pK_A$=−3 and 1.9) and a comparably weak base ($pK_B$=4.75, i.e. $pK_A$=9.25), absolutely requires a regulation of the pH value, otherwise the release of sulfuric acid decreases the pH to a value below 3, sometimes even below 2, which is unfavorable for growth and production. EP 0.845.538 B1 solves this by automatically apportioning 35% sodium hydroxide, which requires considerable additional control measures and may lead to complete failure of fermentation in case of malfunctioning.

A further aspect concerning fermentation for obtaining erythritol relates to the suppression of byproducts such as ribitol and glycerol. In this context, EP 0,845,538 discloses that a higher proportion of complex nitrogen sources (in this case corn steep liquor) stimulates the formation of glycerol. However, limiting the complex growth promoter substances always entails a reduction of the growth and production rates. The procedure according to EP 0,845,538, wherein, in addition to ammonium sulfate, up to 50% corn steep liquor are used as nitrogen source, solves this problem of byproduct formation only insufficiently, as is shown in the examples therein by the fact that glycerol formation cannot be completely suppressed: the amount of glycerol formed varies between approximately 1.9% (Example 5) and 50.2% (Example 12) of the amount of erythritol.

In Biotechnology and Bioengineering of 5 Aug. 2006, p. 899-908, Diano et al. investigated the effects of various parameters, e.g. the nitrogen sources ammonium and nitrate, on the metabolism of *Aspergillus niger*. The pH value was initially set to 3 and then gradually raised to 4.5. The results showed that nitrate, as against ammonium, has a positive impact on the production of some alcohols, e.g. erythritol, by *Aspergillus*.

U.S. Pat. No. 6,030,820 A describes a process for producing high-purity crystalline erythritol from a microbial culture solution as the starting material. A possible microorganism described for obtaining the starting material is *Moniliella tomentosa* var. *pollinis*, and a possible nitrogen source mentioned is ammonium nitrate. Neither this nor the pH value during cultivation are described in detail.

Furthermore, EP 0,327,342 A2 discloses a process for producing erythritol by cultivating microorganisms producing the same, wherein the cell concentration in the fermentation tank is continuously regulated by cycling a part of the culture broth through an external cell separator. Ammonium nitrate is mentioned as a general example for possible nitrogen sources. The only example given for the microorganism is *Aureobasidium* sp. SN-G42, and a pH value for the culture medium (pH 4.2) is only given in the last example, but not mentioned apart from that.

In Biotechnology and Bioprocess Engineering 8(3), 173-178 (2003), Lee, Kwang-Jun et al. describe the improvement of erythritol productivity by cultivating different mutants of *Penicillium*. For one of them, it is mentioned that by adding ammonium carbonate, potassium nitrate and sodium nitrate, the yield of erythritol can be increased considerably. In the CAS abstract, an example of a study with 0.5% yeast extract, 0.5% $(NH_4)_2C_2O_4$ (apparently ammonium oxalate), 0.1% $KNO_3$ and 0.1% $NaNO_3$ as nitrogen sources is given (i.e. among the nitrogen sources, the two nitrates correspond to a weight percentage of below 17% and a proportion of utilizable nitrogen of approximately 15%).

OBJECT OF THE INVENTION

It was thus the object of the invention to provide an improved economic process for producing erythritol in high yield and purity, which process at least reduces or even completely eliminates the above problems regarding the pH value of the culture medium and the formation of byproducts.

DISCLOSURE OF THE INVENTION

This object is achieved by the inventive use of at least one inorganic nitrate in a fermentation process for producing erythritol using a yeast strain of the *Moniliella* species as erythritol-producing microorganism, wherein at least one inorganic nitrate is simultaneously used as main nitrogen source and as pH regulator in the culture medium, as well as by a thus improved method for producing erythritol. In a method according to the invention, a yeast strain of the *Moniliella* species is grown by a known method in a culture medium containing one or more carbon source(s) and one or more nitrogen source(s), wherein at least one inorganic nitrate is used as a nitrogen source in the culture medium, and erythritol is recovered from the medium. In analogy to the inventive use, the method of the invention is characterized by the fact that the at least one inorganic nitrate is simultaneously used as a main nitrogen source and as a pH regulator in the culture medium. The at least one inorganic nitrate is preferably selected from potassium nitrate, sodium nitrate and ammonium nitrate, especially from potassium nitrate and sodium nitrate.

Using the at least one inorganic nitrate as a main nitrogen source thus allows, on the one hand, for the omission of process steps for adjusting the pH because the pH value is regulated by appropriately selecting the type and amount of nitrate and always remains within the optimum range during fermentation without readjustment. On the other hand, the formation of other alcohols, such as glycerol, as byproducts is strongly suppressed and can, in preferred embodiments, be even completely eliminated. The inorganic nitrates used according to the present invention are—as opposed to urea—approved food additives (E251, E252), which are in addition completely degraded during the first 2 to 3 days of fermentation.

Herein, "main nitrogen source" means one that provides at least 20% of the utilizable nitrogen. However, the advantages of the invention are mainly seen when the at least one inorganic nitrate is used in an amount of 30 to 85%, more preferably 45 to 65%, of the total utilizable nitrogen content, wherein the respective optimum amounts also depend on the basicity of the cation.

According to the invention, one or more organic nitrogen sources, e.g. corn steep liquor, yeast extract and mixtures thereof may be used in addition to the at least one inorganic nitrate, even in relatively high proportions, without leading to the formation of undesirable amounts of byproducts. Contrary to prior teachings, it has been found that increasing concentrations of corn steep liquor lead to a reduction of the proportion of byproducts. When using inorganic nitrates according to the invention, the proportion of the complex nitrogen source may be optimally adapted to the requirements of the fermentation, i.e. highest possible productivity and yield, as well as to those of product isolation, e.g. as little interfering components and byproducts as possible.

According to the invention, the microorganisms used are members of the *Moniliella* species, preferably a strain of *Moniliella tomentosa*, even more preferably a strain of the *pollinis* variety, in order to obtain erythritol in the highest possible yield and purity due to the especially good effect of the invention with these fungi.

The present invention will now be described with reference to examples, which are provided for illustration only and not for limitation of the invention.

EXAMPLES

Example 1

100 ml of a preculture medium consisting of

| | |
|---|---|
| 15% | glucose |
| 0.4% | $KNO_3$ |
| 0.1% | yeast extract |
| 0.8% | corn steep liquor |
| 10 ppm | $MnSO_4 \cdot H_2O$ |
| 2 ppm | thiamine hydrochloride | were adjusted to pH 3.6 with citric acid and sterilized in a 500 ml round bottom flask for 20 min at 110° C. The flask cooled to 30° C. was inoculated with *Moniliella tomentosa* var. *pollinis* from a glycerol can and shaken for 24 hours at 30° C. and 200 $min^{-1}$.

1 ml of this preculture was inoculated into 100 ml of a production medium consisting of

| | |
|---|---|
| 35% | glucose |
| 0.35% | $KNO_3$ |
| 0.05% | yeast extract |
| 0.40% | corn steep liquor |
| 0.025% | $KH_2PO_4$ |
| 5 ppm | $MnSO_4 \cdot H_2O$ |
| 3 ppm | Thiamine hydrochloride. |

Prior to the inoculation, the medium was adjusted to pH 3.6 with citric acid in four 500 ml shake flasks, sterilized for 20 min at 110° C. and set to a temperature of 30° C. The flasks were shaken for 9 days at 200 $min^{-1}$. During fermentation, sterile samples were taken and analyzed by HPLC. In this example, 62% of the total utilizable nitrogen content of the medium were added in the form of potassium nitrate.

Below, the results of the HPLC analysis for the four flasks after 0, 42, 116, 165 and 210 hours of fermentation are shown.

| Time (h) | % glucose | % erythritol | pH | Time (h) | % glucose | % erythritol | pH |
|---|---|---|---|---|---|---|---|
| | Flask 1 | | | | Flask 2 | | |
| 0 | 35.00 | 0.00 | 3.60 | 0 | 35.00 | 0.00 | 3.60 |
| 42 | 27.86 | 0.36 | 5.24 | 42 | 27.99 | 0.35 | 5.24 |
| 116 | 12.11 | 7.06 | 4.25 | 116 | 12.92 | 7.44 | 4.26 |
| 165 | 4.23 | 12.80 | 3.95 | 165 | 4.54 | 12.87 | 3.96 |
| 210 | 0.00 | 13.71 | 4.00 | 210 | 0.00 | 14.52 | 4.01 |
| | Flask 3 | | | | Flask 4 | | |
| 0 | 35.00 | 0.00 | 3.60 | 0 | 35.00 | 0.00 | 3.60 |
| 42 | 27.86 | 0.37 | 5.22 | 42 | 27.32 | 0.36 | 5.24 |
| 116 | 12.90 | 7.59 | 4.27 | 116 | 12.75 | 7.66 | 4.26 |
| 165 | 4.29 | 13.04 | 3.97 | 165 | 3.96 | 12.66 | 3.97 |
| 210 | 0.00 | 15.25 | 4.04 | 210 | 0.00 | 14.26 | 4.04 |

The mean erythritol content of the four flasks was 14.4%. The pH value remained within the optimum range of 3 to 6 during the entire fermentation without addition of any bases.

Comparative Example 1

The experiment from example 1 was repeated with the production medium containing 0.23% $(NH_4)_2SO_4$ instead of 0.35% $KNO_3$. The proportion of inorganic nitrogen was maintained equal in the two experiments at approximately 0.05% and corresponded to 62% of the total utilizable nitrogen amount.

| Time (h) | % glucose | % erythritol | pH | Time (h) | % glucose | % erythritol | pH |
|---|---|---|---|---|---|---|---|
| | Flask 1 | | | | Flask 2 | | |
| 0 | 35.00 | 0.00 | 3.60 | 0 | 35.00 | 0.00 | 3.60 |
| 42 | 28.75 | 0.31 | 2.15 | 42 | 30.62 | 0.29 | 2.11 |
| 116 | 26.19 | 1.13 | 2.00 | 116 | 25.13 | 0.90 | 1.96 |
| 165 | 25.18 | 1.26 | 2.01 | 165 | 25.18 | 0.93 | 1.97 |
| 210 | 26.77 | 1.47 | 1.99 | 210 | 22.82 | 0.85 | 1.95 |
| | Flask 3 | | | | Flask 4 | | |
| 0 | 35.00 | 0.00 | 3.60 | 0 | 35.00 | 0.00 | 3.60 |
| 42 | 26.41 | 0.28 | 2.12 | 42 | 30.93 | 0.31 | 2.12 |
| 116 | 25.69 | 0.98 | 1.96 | 116 | 24.52 | 0.95 | 1.94 |
| 165 | 28.37 | 1.07 | 1.98 | 165 | 26.83 | 1.06 | 1.98 |
| 210 | 21.50 | 0.84 | 1.96 | 210 | 26.90 | 1.06 | 1.93 |

As is shown by the results above, the pH value drops to values of approximately 2 or less during the growth phase due to the assimilation of ammonium. Production without pH regulation is thus not possible. The amounts of erythritol formed are correspondingly low and amount to approximately 1/10 of those in inventive Example 1 at best.

Example 2

Example 1 was repeated with the amounts of corn steep liquor (CSL) (0.40%) and potassium nitrate (0.35%) from Example 1 each maintained the same, doubled as well as halved. After 10 days, the concentrations of glycerol and ribitol as well as the yield of erythritol, in relation to the glucose used, were determined. Each experiment was performed in duplicate, the mean values of which are shown below.

| $KNO_3$/CSL | 0.20% | 0.40% | 0.80% | $KNO_3$/CSL | 0.20% | 0.40% | 0.80% |
|---|---|---|---|---|---|---|---|
| | Glycerol (%) | | | | Ribitol (%) | | |
| 0.18% | 6.63 | 4.68 | 0.00 | 0.18% | 3.66 | 3.88 | 0.80 |
| 0.35% | 3.31 | 0.70 | 0.00 | 0.35% | 2.32 | 2.26 | 0.36 |
| 0.70% | 0.78 | 0.00 | 0.00 | 0.70% | 0.16 | 0.15 | 0.16 |
| | Yield of erythritol (%) | | | | Productivity (g/l · h) | | |
| 0.18% | 26.0 | 38.1 | 49.8 | 0.18% | 0.55 | 0.96 | 1.21 |
| 0.35% | 42.5 | 50.0 | 50.1 | 0.35% | 0.88 | 1.06 | 1.38 |
| 0.70% | 42.3 | 45.7 | 44.0 | 0.70% | 0.96 | 1.27 | 1.31 |

It is obvious that, when inorganic nitrate is used as a main nitrogen source, increasing amounts of corn steep liquor allow for a suppression of byproduct formation and an increase of the yield at the same time. With the inventive method, glycerol as a byproduct can be completely avoided while the amount of ribitol can be kept far below 1%. In addition, productivity rises considerably when more nitrogen is added.

Example 3

50 ml of a preculture as described in Example 1 were inoculated into a 3 liter fermenter with a medium consisting of

| | |
|---|---|
| 34% | glucose |
| 0.20% | KNO$_3$ |
| 0.08% | NH$_4$NO$_3$ |
| 0.05% | yeast extract |
| 0.30% | corn steep liquor |
| 0.025% | KH$_2$PO$_4$ |
| 3 ppm | MnSO$_4$•H$_2$O |
| 3 ppm | thiamine hydrochloride. |

The fermentation was performed at a temperature of 28° C. without pH regulation. Aeration was 0.18 vvm at a stirrer rotational speed of 500 rpm$^{-1}$. After the glucose was consumed, the following results were found:

| | |
|---|---|
| erythritol | 16.11% |
| ribitol | 0.26% |
| glycerol | 0.00% |
| pH value | 3.57. |

Consequently, it was proven that part of the potassium nitrate can be replaced by other inorganic nitrates without interfering with the advantages of the invention described above and evidenced by measured values.

Example 4

80 liters of a preculture as described in Example 1 were inoculated into a 3,000 liter bubble column with 2,600 liters of a medium consisting of

| | |
|---|---|
| 23.01% | glucose |
| 17.25% | fructose |
| 0.35% | KNO$_3$ |
| 0.05% | yeast extract |
| 0.40% | corn steep liquor |
| 0.025% | KH$_2$PO$_4$ |
| 5 ppm | MnSO$_4$•H$_2$O |
| 3 ppm | thiamine hydrochloride. |

The temperature was adjusted to 30° C. Aeration was set to 0.19 vvm. After the sugar was completely consumed, the following results were found:

| | |
|---|---|
| erythritol | 19.96% |
| ribitol | 0.18% |
| glycerol | 1.96% |
| pH value (mean) | 4.48 |
| yield of erythritol | 49.4%. |

The pH value varied between 4.35 and 4.62 and was thus within the optimum range without any regulation. At no point during fermentation, the addition of an antifoaming agent was necessary. Consequently, this example shows that other carbon sources than glucose can be utilized with the same efficiency in the method of the invention using inorganic nitrogen as a main nitrogen source.

In summary, by using at least one inorganic nitrate as a main nitrogen source as well as a pH regulator, the present invention thus provides methods for producing erythritol, by means of which the desired product can by recovered in high yield and purity as well as in an economic manner: a) process steps for regulating the pH value may be completely omitted; b) very low amounts of interfering byproducts are formed, which strongly facilitates erythritol isolation; c) productivity can be increased considerably; and d) the inorganic nitrates used are commercially available at low prices. Consequently, there is no doubt at all about the industrial applicability of the invention.

The invention claimed is:

1. A method for producing erythritol, which comprises growing a yeast strain of the *Moniliella tomentosa* species in a culture medium containing one or more carbon source(s) and one or more nitrogen source(s), wherein at least one inorganic nitrate is used as a nitrogen source in the culture medium, as well as recovering erythritol from the medium, characterized in that the at least one inorganic nitrate is simultaneously used as a main nitrogen source providing at least 20% of the total utilizable nitrogen content and as a pH regulator in the culture medium.

2. The method according to claim 1, characterized in that the at least one inorganic nitrate is selected from potassium nitrate, sodium nitrate and ammonium nitrate.

3. The method according to claim 2, characterized in that the at least one inorganic nitrate is selected from potassium nitrate and sodium nitrate.

4. The method according to any one of the preceding claims 1, 2, and 3 characterized in that the at least one inorganic nitrate is used in an amount of 30 to 85% of the total utilizable nitrogen content.

5. The method according to claim 4, characterized in that the at least one inorganic nitrate is used in an amount of 45 to 65% of the total utilizable nitrogen content.

6. The method according to any one of the preceding claims 1, 2, and 3 characterized in that, in addition to the at least one inorganic nitrate, an organic nitrogen source is used as a further nitrogen source.

7. The method according to claim 6, characterized in that corn steep water and/or yeast extract are/is used as (a) further nitrogen source(s).

8. The method according to any one of the preceding claims 1, 2, and 3 characterized in that a strain of *Moniliella tomentosa* of the *pollinis* variety is used.

* * * * *

UNITED STATES PATENT AND TRADEMARK OFFICE
CERTIFICATE OF CORRECTION

PATENT NO. : 8,187,847 B2  
APPLICATION NO. : 12/443060  
DATED : May 29, 2012  
INVENTOR(S) : Edlauer et al.

Page 1 of 1

It is certified that error appears in the above-identified patent and that said Letters Patent is hereby corrected as shown below:

In Column 4, Example 1:

Column 4, Line 19, reads "0.8%  corn steep liquor"
                should read -- 0.6%  corn steep liquor --

Signed and Sealed this
Tenth Day of July, 2012

David J. Kappos
*Director of the United States Patent and Trademark Office*